United States Patent
Takahashi

(10) Patent No.: US 8,251,988 B2
(45) Date of Patent: Aug. 28, 2012

(54) ULTRASONIC TREATMENT APPARATUS

(75) Inventor: Hiroyuki Takahashi, Akishima (JP)

(73) Assignee: Olympus Medical Systems Corp., Tokyo (JP)

( * ) Notice: Subject to any disclaimer, the term of this patent is extended or adjusted under 35 U.S.C. 154(b) by 1548 days.

(21) Appl. No.: 11/417,356

(22) Filed: May 3, 2006

(65) Prior Publication Data

US 2006/0258975 A1 Nov. 16, 2006

(30) Foreign Application Priority Data

May 13, 2005 (JP) .................................. 2005-141535

(51) Int. Cl.
*A61B 18/04* (2006.01)
(52) U.S. Cl. .......................................... 606/34; 606/169
(58) Field of Classification Search ................... 606/34, 606/169

See application file for complete search history.

(56) References Cited

U.S. PATENT DOCUMENTS

| | | | | |
|---|---|---|---|---|
| 5,707,402 A | * | 1/1998 | Heim | 607/88 |
| 5,997,528 A | * | 12/1999 | Bisch et al. | 606/1 |
| 6,156,036 A | * | 12/2000 | Sussman et al. | 606/48 |
| 6,666,860 B1 | * | 12/2003 | Takahashi | 606/34 |
| 2001/0029315 A1 | * | 10/2001 | Sakurai et al. | 600/101 |
| 2002/0058933 A1 | * | 5/2002 | Christopherson et al. | 606/34 |

FOREIGN PATENT DOCUMENTS

JP 2001-178734 7/2001

* cited by examiner

*Primary Examiner* — Michael Peffley
*Assistant Examiner* — Daniel Fowler
(74) *Attorney, Agent, or Firm* — Scully, Scott, Murphy & Presser, P.C.

(57) ABSTRACT

An ultrasonic treatment apparatus includes an ultrasonic instrument, a fluid irrigation unit, a fluid suction unit, an ultrasonic driving control unit, and an irrigation/suction control unit. The ultrasonic instrument treats a living-body tissue through ultrasonic vibrations. The fluid irrigation unit supplies a cooling fluid for cooling the ultrasonic instrument to the ultrasonic instrument. The fluid suction unit sucks a cooling fluid irrigated by the fluid irrigation unit to the ultrasonic instrument. The ultrasonic driving control unit controls the driving of ultrasonic vibrations of the ultrasonic instrument. The irrigation/suction control unit sequentially controls the driving of the fluid irrigation unit and the driving of the fluid suction unit in accordance with the output of the ultrasonic driving control unit.

9 Claims, 5 Drawing Sheets

ULTRASONIC TREATMENT APPARATUS

This application claims benefit of Japanese Application No. 2005-141535 filed in Japan on May 13, 2005, the contents of which are incorporated by this reference.

BACKGROUND OF THE INVENTION

1. Field of the Invention

The present invention relates to an ultrasonic treatment apparatus for giving an ultrasonic treatment.

2. Description of the Related Art

In recent years, electric treatment apparatus have been widely employed such as an electric knife apparatus for giving a medical treatment by applying high-frequency current and an ultrasonic treatment apparatus for giving a medical treatment by applying ultrasonics.

For example, an electric treatment system disclosed in Japanese Unexamined Patent Application Publication No. 2001-178734 identifies the type of a treatment instrument to be used in combination between/among multiple electric medical apparatuses, and performing appropriate control over the treatment instrument by the electric medical apparatuses.

When an ultrasonic coagulating/cutting instrument is connected thereto, ultrasonics output therefrom simultaneously and interlockingly causes smoke extraction from a pneumoperitoneum. Further in the disclosure, when an ultrasonic suction instrument is connected thereto, ultrasonics output therefrom simultaneously and interlockingly causes operation of an irrigation device and a suction device.

The ultrasonic coagulating/cutting instrument in the electric treatment system coagulates and cuts simultaneously, and the treating unit grasps a tissue and apply ultrasonic vibrations to the tissue. As a result, the friction heat in the grasped part denatures the tissue so that the coagulation and cutting can be simultaneously performed thereon.

The temperature of the treating unit is functionally high immediately after the ultrasonic coagulating/cutting instrument performs the ultrasonics output.

SUMMARY OF THE INVENTION

One aspect of the present invention includes an ultrasonic instrument which treats a living-body tissue through ultrasonic vibrations, a fluid irrigation unit which supplies a cooling fluid to the ultrasonic instrument for cooling the ultrasonic instrument, a fluid suction unit which sucks the cooling fluid irrigated by the fluid irrigation unit to the ultrasonic instrument, an ultrasonic driving control unit which controls the driving of ultrasonic vibrations of the ultrasonic instrument, and a fluid irrigation/suction control unit which controls sequentially the driving of the fluid irrigation unit and the driving of the fluid suction unit in accordance with the output of the ultrasonic driving control unit.

DETAILED DESCRIPTION OF THE PREFERRED EMBODIMENTS

Embodiments of the present invention will be described with reference to drawings.

[First Embodiment]

Figure 1:
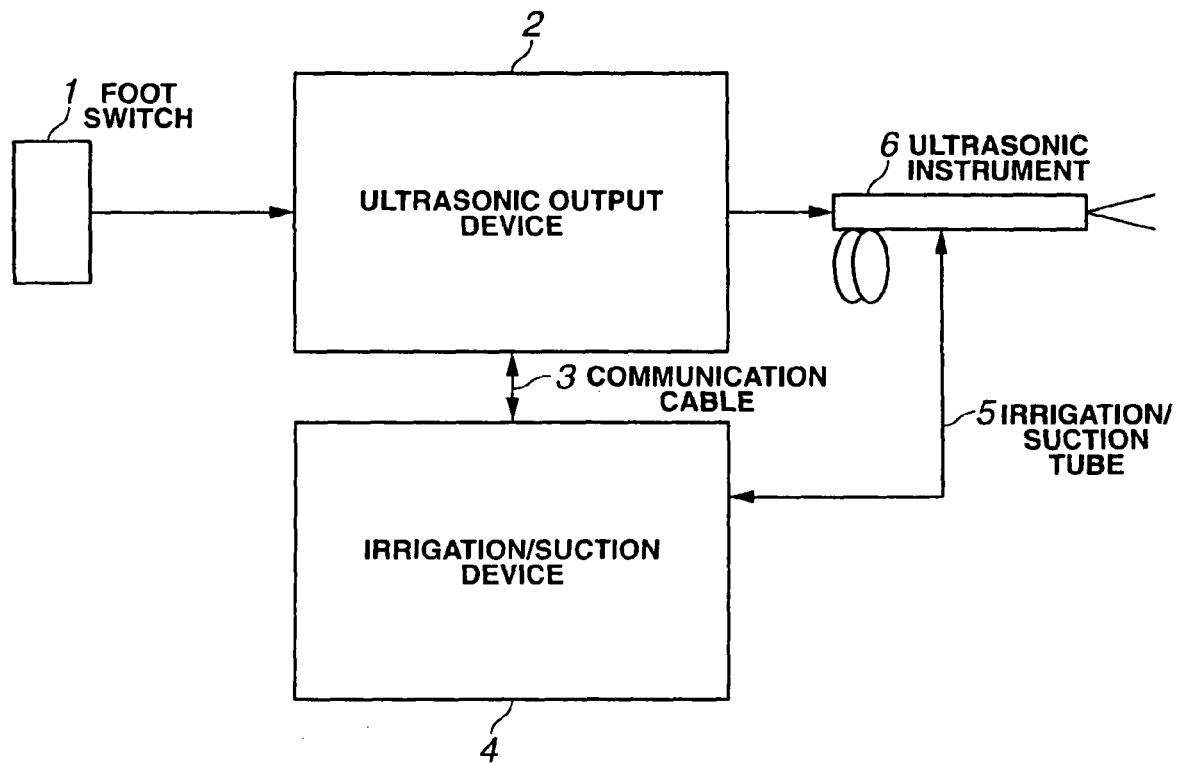
FIG. 1 is an entire construction diagram of an ultrasonic treatment apparatus according to a first embodiment of the present invention.

FIG. 1 is an entire construction diagram of an ultrasonic treatment apparatus according to a first embodiment of the present invention.

In FIG. 1, the ultrasonic treatment apparatus includes a foot switch 1, an ultrasonic output device 2, a communication cable 3, an irrigation/suction device 4, an irrigation/suction tube 5 and an ultrasonic instrument 6.

An operator can control ON/OFF of the ultrasonic output by stepping a pedal, not shown, of the foot switch 1.

An ON/OFF signal from the foot switch 1 is input to the ultrasonic output device 2. Based on the ON signal, the ultrasonic output device 2 transmits ultrasonics output to the ultrasonic instrument 6 connecting to the ultrasonic output device 2. The ultrasonic instrument 6 treats a living-body tissue through ultrasonic vibrations.

In the ultrasonic instrument 6, electric energy is converted to mechanical energy by the ultrasonic output from the ultrasonic output device 2, and a treating unit provided at the end of the ultrasonic instrument 6 ultrasonically vibrates for performing a coagulating/cutting treatment on a living-body tissue.

Furthermore, the ultrasonic output device 2 is connected to the irrigation/suction device 4 via the communication cable 3, so that signals such as a control signal on the availability of the interlocking can be exchanged.

The irrigation/suction device 4 receives a signal from the ultrasonic output device 2 via the communication cable 3 for performing irrigation, suction and the control.

The irrigation/suction tube 5 connecting to the irrigation/suction device 4 is connected to the ultrasonic instrument 6.

The irrigation/suction tube 5 may be used to control the irrigation/suction of the ultrasonic instrument 6 under the control of the irrigation/suction device 4.

Figure 2:
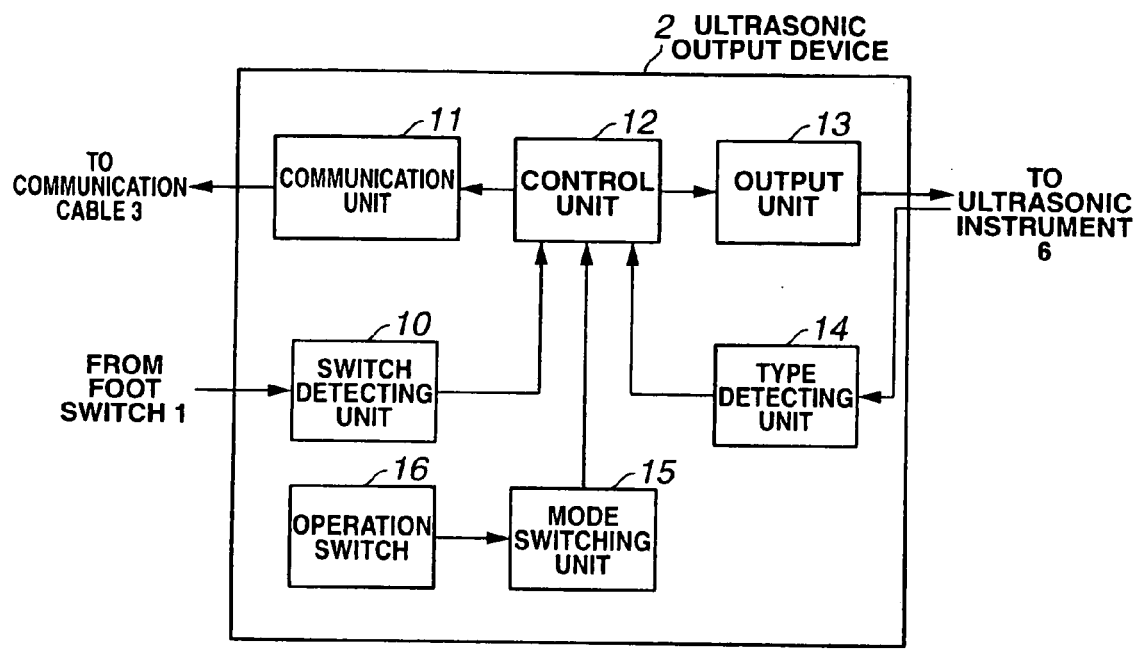
FIG. 2 is a block diagram showing a construction of an ultrasonic output device in FIG. 1.

FIG. 2 shows a construction of the ultrasonic output device 2 in FIG. 1.

In FIG. 2, the ultrasonic output device 2 includes a switch detecting unit 10, a communication unit 11, a control unit 12, an output unit 13, a type detecting unit 14 and a mode switching unit 15.

The control unit 12 functions as an ultrasonic driving control unit for controlling the driving of ultrasonic vibrations of the ultrasonic instrument 6.

When the foot switch 1 is connected to the ultrasonic output device 2, the signal of the foot switch 1 is input to the switch detecting unit 10. The switch detecting unit 10 always detects the ON/OFF state of the foot switch 1.

Figure 4:
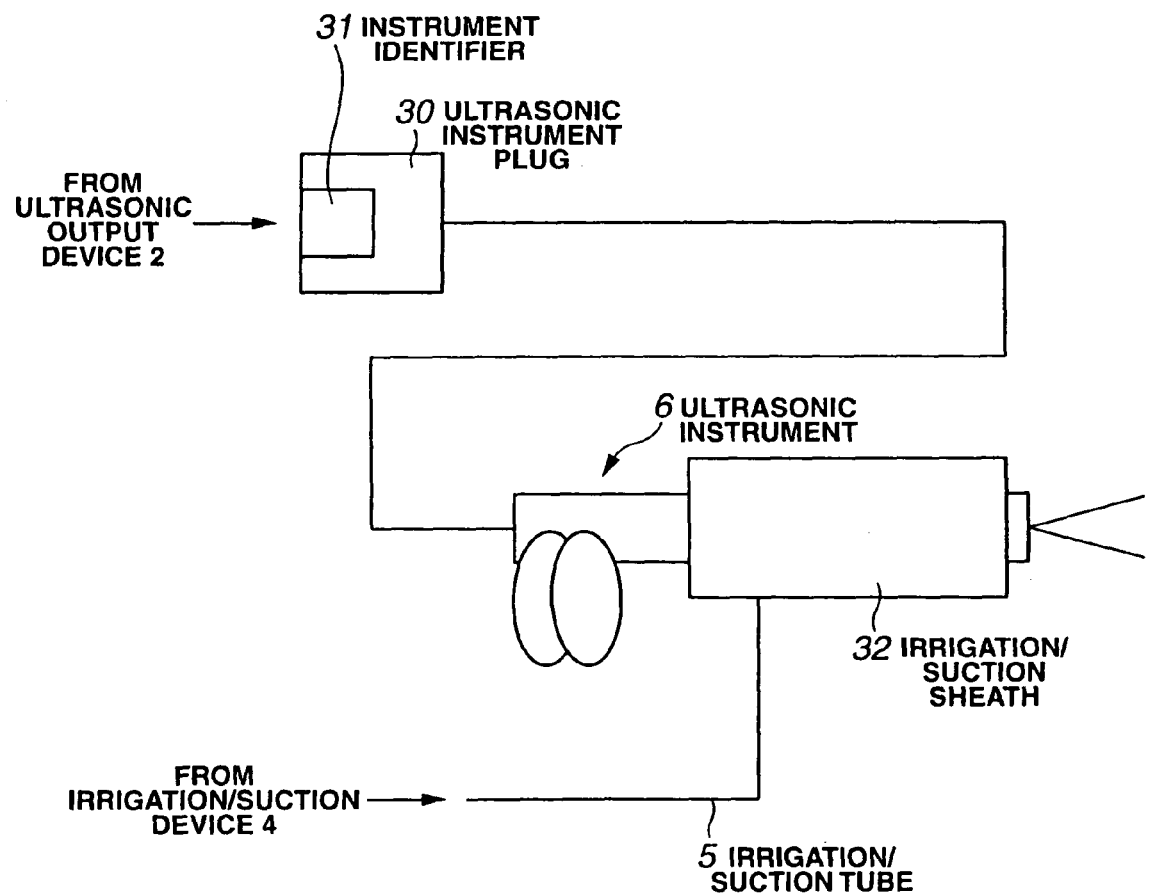
FIG. 4 is a diagram showing a construction required for the ultrasonic instrument in FIG. 1.

When the ultrasonic instrument 6 is connected to the ultrasonic output device 2, the type detecting unit 14 receives the information on an instrument identifier 31 attached to an ultrasonic instrument plug 30 shown in FIG. 4 and decodes the type of the ultrasonic instrument 6.

The decoded data is input from the type detecting unit 14 to the control unit 12, and, in the control unit 12, the data from the type detecting unit 14 is used as a setting condition for a driving frequency, driving current and driving voltage, which are parameters for driving the ultrasonic instrument 6, and/or as a determination condition for detecting an abnormality.

Furthermore, in the control unit 12, the data from the type detecting unit 14 is also used as a condition for determining the availability of the interlocking of the irrigation/suction device 4, which will be described later.

The mode switching unit 15 functioning as a select unit has an operation switch 16 functioning as an external input unit. When the operation switch 16 is pressed, the mode switching unit 15 can select either an irrigation/suction interlocking mode or an irrigation/suction non-interlocking mode (normal mode).

The mode switching unit 15 identifies the state of the operation switch 16 and informs the availability of the interlocking to the control unit 12.

In accordance with the availability of the interlocking setting by the mode switching unit 15, the ultrasonic output device 2 transmits the information on the availability of the interlocking to the irrigation/suction device 4 through the communication unit 11 and the communication cable 3.

The output unit 13 outputs and supplies ultrasonics to the ultrasonic instrument 6 under the control of the control unit 12.

Figure 3:
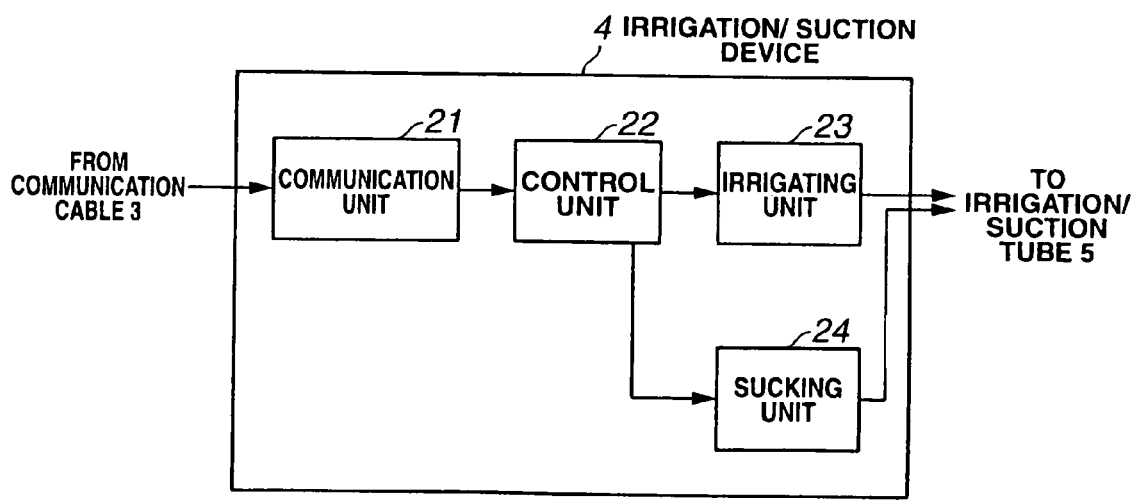
FIG. 3 is a block diagram showing a construction of an irrigation/suction device in FIG. 1.

FIG. 3 shows a construction of the irrigation/suction device 4 in FIG. 1.

In FIG. 3, the irrigation/suction device 4 includes a communication unit 21, a control unit 22, an irrigating portion 23 and a sucking unit 24.

The control unit 22 functions as an irrigation/suction control unit for sequentially controlling the driving of fluid irrigation and the driving of fluid suction of the irrigation/suction device 4 in accordance with the output from the control unit 12 functioning as the ultrasonic driving control unit.

The communication unit 21 receives information on the availability of the interlocking from the ultrasonic output device 2 via the communication cable 3.

Based on the availability of the interlocking information received by the communication unit 21, the control unit 22 controls the irrigation by the irrigating portion 23 functioning as a fluid irrigation unit and controls the suction by the sucking unit 24 functioning as a fluid suction unit.

The irrigating portion 23 irrigates water to an irrigation duct of the irrigation/suction tube 5, and the sucking unit 24 sucks from a suction duct of the irrigation/suction tube 5.

Based on the information on the instrument identifier 31 attached to the ultrasonic instrument 6, the control unit 22 can control the availability of the interlocking of the irrigation and suction.

FIG. 4 shows a construction required for the ultrasonic instrument 6 in FIG. 1.

The ultrasonic instrument 6 and the ultrasonic output device 2 are connected via an ultrasonic instrument plug 30. The ultrasonic instrument plug 30 has the instrument identifier 31, and, when the ultrasonic instrument plug 30 is connected to the ultrasonic output device 2, the control unit 12 of the ultrasonic output device 2 automatically decodes what type of ultrasonic instrument 6 is connected thereto by using the type detecting unit 14.

Desirably, the instrument identifier 31 is favorably a part such as a resister and a non-volatile memory.

The ultrasonic output from the ultrasonic output device 2 is transmitted to the ultrasonic instrument 6 via the ultrasonic instrument plug 30 and a cable connected thereto.

The ultrasonic instrument 6 internally has an ultrasonic vibrator (such as a piezoelectric element) for converting electric energy to mechanical energy, that is, ultrasonic vibrations, and the treating unit at the end of the ultrasonic instrument 6 ultrasonically vibrates.

An irrigation/suction sheath 32 is connectable to the ultrasonic instrument 6, and the irrigation/suction sheath 32 has an irrigation/suction connection port, not shown, to which the irrigation/suction tube 5 is connectable.

Thus, the irrigation/suction device 4 may be used to perform irrigation and suction from the end of the ultrasonic instrument 6.

Figure 5:
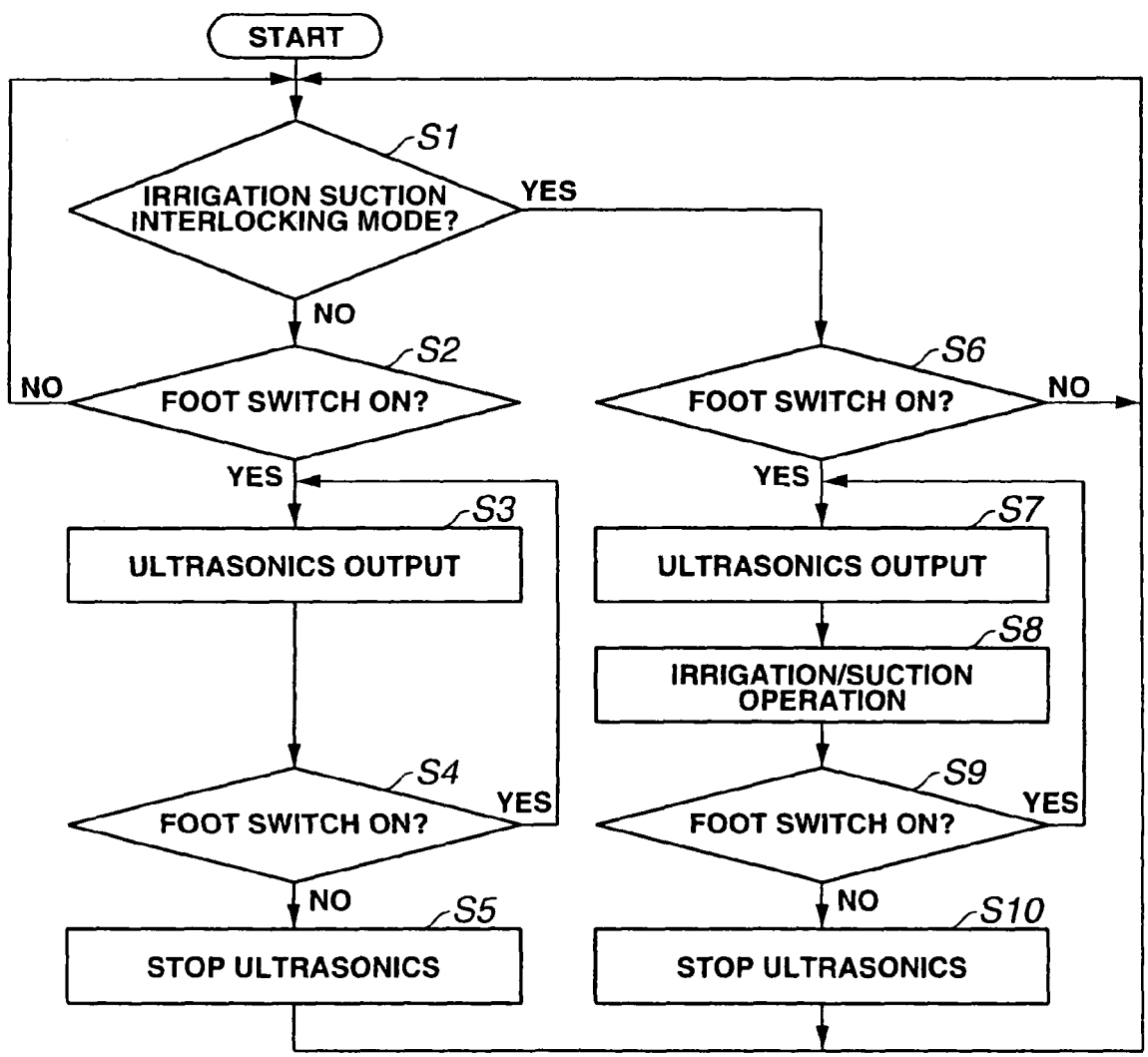
FIG. 5 is a flowchart describing an operation of the ultrasonic treatment apparatus in FIG. 1.

FIG. 5 is a flowchart describing an operation of the ultrasonic treatment apparatus in FIG. 1.

Either irrigation/suction interlocking mode or not is selected through the mode switching unit 15 of the ultrasonic output device 2 (step S1).

If the irrigation/suction interlocking mode is not selected, the same operation flow as that of a conventional ultrasonic instrument is adopted.

If the irrigation/suction interlocking mode is not selected, the ultrasonic output device 2 always detects the ON/OFF state of the foot switch 1 (step S2). When turned on, an ultrasonic output occurs (step S3).

Then, the ON/OFF state is always detected until the foot switch 1 is turned off (step S4). When turned off, the ultrasonics output stops (step S5).

On the other hand, when the irrigation/suction interlocking mode is selected, the irrigation/suction device 4 synchronously interlocks with the operation of the ultrasonic output device 2 (step S1), which is a characteristic of the present invention.

Also, in this case, the ON/OFF state of the foot switch 1 is always detected (step S6), and, when turned on, ultrasonics output occurs (step S7).

Furthermore, the state is informed from the ultrasonic output device 2 to the irrigation/suction device 4, and a prescribed interlocking operation is performed, which will be described later (step S8).

Then, the ON/OFF state is always detected until the foot switch 1 is turned off (step S9), and, when turned off, the ultrasonics output stops (step S10).

Figure 6:
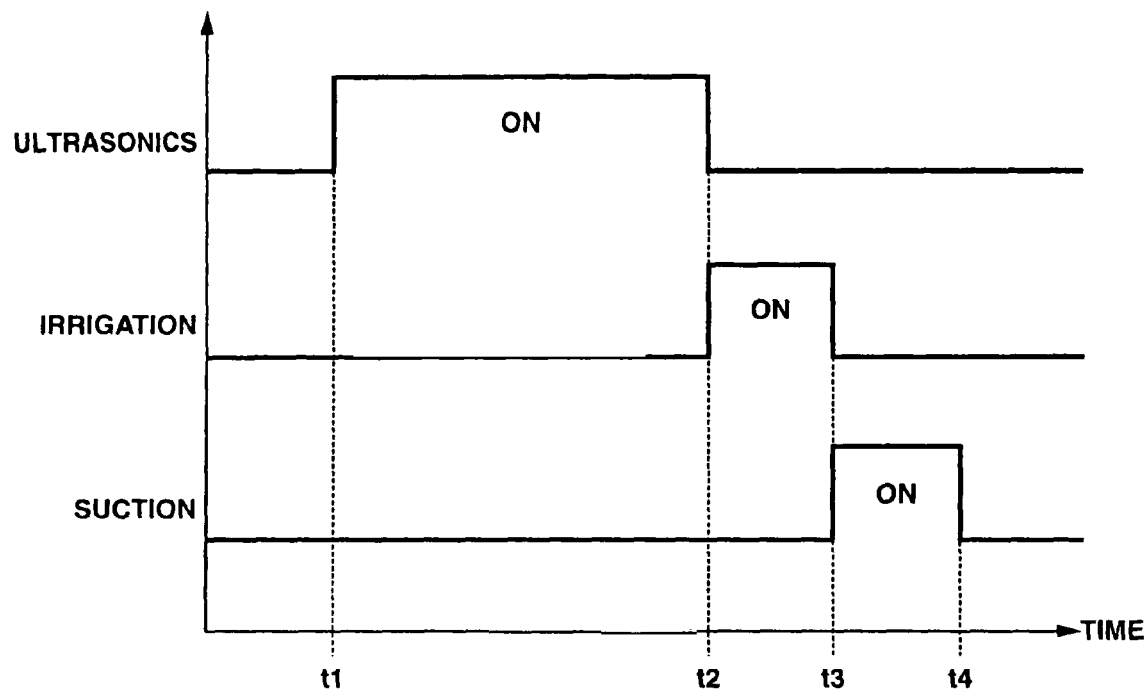
FIG. 6 is a timing chart showing an interlocking operation of the irrigation/suction device in FIG. 1.

FIG. 6 is a timing chart showing an interlocking operation of the irrigation/suction device 4 in FIG. 1. That is, the timing chart describes an operation to be performed when the irrigation/suction interlocking is selected by the ultrasonic output device 2.

At time t1, the foot switch 1 is turned on, and ultrasonics output occurs from the ultrasonic output device 2.

In this case, since the heat generated by ultrasonic vibrations denatures and coagulates and/or cuts a tissue for coagulating/cutting, the irrigation, which might interfere with it, is terminated.

At time t2, the foot switch 1 is turned off, and the ultrasonics output from the ultrasonic output device 2 stops.

Then, irrigation is performed by the irrigation/suction device 4 in order to cool the treating unit at the distal end of the ultrasonic instrument 6, the temperature of which has been increased by the ultrasonic vibrations. The irrigation is performed for a preset and predetermined period of time so that the treating unit can be cooled to a prescribed temperature. The irrigation liquid may be generally physiological saline. In order to hit the irrigation fluid to the end of the ultrasonic instrument 6 properly, the suction by the irrigation/suction device 4 is terminated.

At time t3 after a lapse of a predetermined period of time from time t2, the irrigation by the irrigation/suction device 4 stops, and the suction is performed by the irrigation/suction device 4 in order to remove the irrigation liquid adhered at the end of the ultrasonic instrument 6.

At time t4, the suction by the irrigation/suction device 4 stops.

Next, a variation example of the embodiment above will be described.

In the embodiment above, the operation switch 16 attached to the mode switching unit 15 is adopted as a parameter for determining the availability of the interlocking of the irrigation/suction device 4. The merit of the use of the mode switching unit 15 for the interlocking between irrigation and suction in the embodiment is that the ultrasonic instrument 6 does not have to be an irrigation-suction interlocking instrument but the ultrasonic instrument 6 is usable by attaching the irrigation/suction sheath 32 to the ultrasonic instrument 6 and selecting the irrigation-suction interlocking through the mode switching unit 15. In other words, there is general versatility that the existing ultrasonic instrument 6 is usable.

On the other hand, as a parameter for determining the availability of the interlocking of the irrigation/suction device 4, the instrument identifier 31 attached to the ultrasonic instrument plug 30 of the ultrasonic instrument 6 may be decoded so that the automatic control can be achieved.

In other words, by decoding unique information of the instrument identifier 31 by the type detecting unit 14 attached to the ultrasonic output device 2, the control unit 12 can automatically determine whether the irrigation/suction device 4 is to be interlocked or not.

In this way, the use of the instrument identifier 31 advantageously provides a useful device including an auto-setup function, which does not require a user to perform various settings though it is an instrument dedicated to the irrigation/suction interlock.

Figure 7:
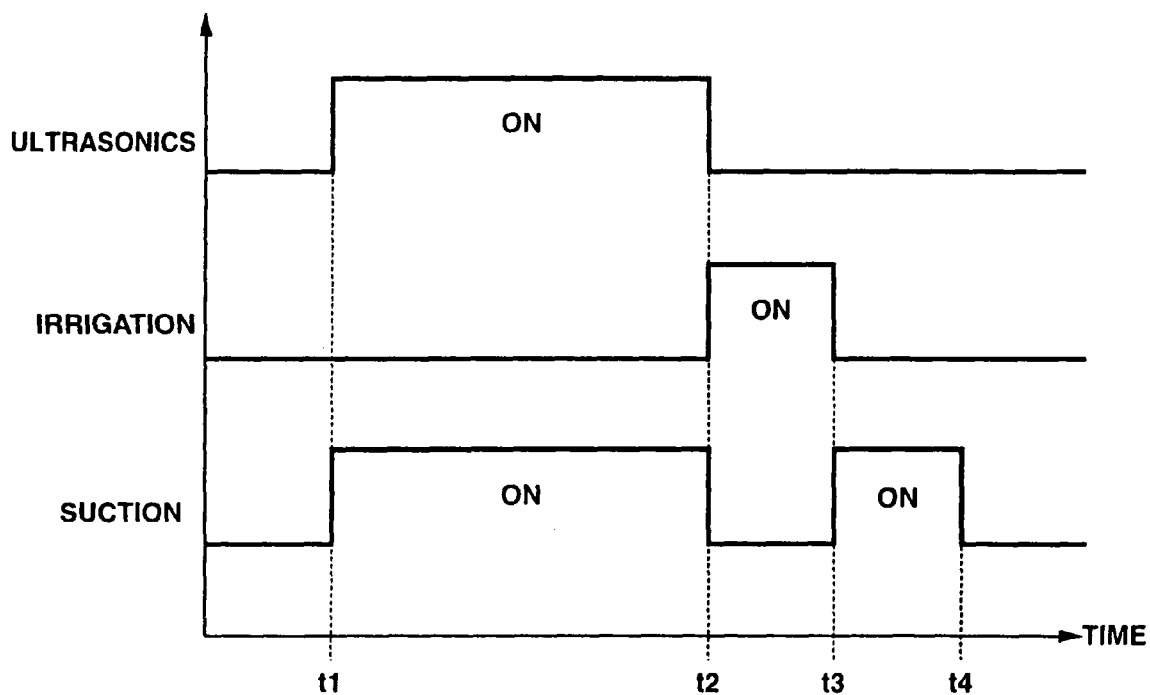
FIG. 7 is a timing chart showing a variation example of the irrigation/suction operation in FIG. 6.

FIG. 7 is a timing chart showing a variation example of the irrigation/suction operation in FIG. 6.

The variation example is different from the irrigation/suction operation in FIG. 6 in the suction operation. That is, the suction operation is performed also at the period between times t1 and t2 when the ultrasonic output device 2 outputs.

Since a tissue is coagulated/cut when the ultrasonic instrument 6 ultrasonically vibrates, the fragments fly.

The suction at the period between times t1 and t2 is performed for capturing the flying fragments of a tissue. Until the period between times t2 and t3, the suction stops in order to efficiently hit the irrigation liquid to the treating unit at the end of the ultrasonic instrument 6. Then, until the period between times t3 to t4, the suction is performed in order to remove the cooling liquid adhered to the distal end and remaining fragments of a tissue.

Desirably, the time for cooling is favorably 2 to 10 seconds. Furthermore, the time when the irrigation/suction device 4 irrigates may be automatically increased for a larger amount of ultrasonics output and a longer time of ultrasonics output since the amount of heat generated at the distal end of the ultrasonic instrument 6 depends on the magnitude of vibrations of the ultrasonic instrument 6 and the time for ultrasonics output.

Having described the irrigation/suction device combining both irrigation and suction functions, they may be in separate devices according to the present invention. The cooling only requires the irrigation device, and, apparently, the irrigation device can decrease the temperature at the distal end of the ultrasonic instrument 6. Furthermore, the irrigation time may be configured to be properly adjustable by a user.

The use of an air supply unit as an alternative of the sucking unit described in this embodiment provides the same effect that the cooling fluid adhered at the end of an instrument can be removed.

According to the above-described first embodiment, an ultrasonic treatment apparatus can quickly reduce the treating unit temperature generated when an ultrasonic instrument for ultrasonic coagulation/cutting is used, and can improve the usability. Furthermore, an ultrasonic treatment apparatus or operation system, which can appropriately implement the interlocking between an ultrasonic instrument and an irrigation/suction device, can be efficiently driven.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasonic treatment apparatus comprising:
    an ultrasonic instrument configured to treat a living-body tissue through ultrasonic vibrations;
    a fluid irrigation unit configured to irrigate a cooling fluid for cooling the ultrasonic instrument to the ultrasonic instrument;
    a fluid suction unit configured to suck the cooling fluid irrigated by the fluid irrigation unit to the ultrasonic instrument;
    an ultrasonic driving control unit configured to control the driving of ultrasonic vibrations of the ultrasonic instrument;
    a mode switching unit configured to select either an irrigation/suction interlocking mode or an irrigation/suction non-interlocking mode; and
    an irrigation/suction control unit configured to sequentially control the driving of the fluid irrigation unit and the driving of the fluid suction unit after a driving output from the ultrasonic driving control unit has stopped when the irrigation/suction interlocking mode is selected, or when the ultrasonic instrument is an instrument capable of irrigating and sucking the cooling fluid, and configured to not perform the driving of the fluid irrigation unit and the driving of the fluid suction unit after a driving output of the ultrasonic driving control unit has stopped when the irrigation/suction non-interlocking mode is selected, or when the ultrasonic instrument is an instrument incapable of irrigating and sucking the cooling fluid.

2. The ultrasonic treatment apparatus according to claim 1, wherein the irrigation/suction control unit is configured to sequentially drive the fluid irrigation unit and the fluid suction unit for a predetermined period of time in accordance with the driving output from the ultrasonic driving control unit for controlling the driving of the ultrasonic instrument when the irrigation/suction interlocking mode is selected or when the ultrasonic instrument is an instrument capable of irrigating and sucking the cooling fluid.

3. The ultrasonic treatment apparatus according to claim 1, wherein the irrigation/suction control unit is configured to control so that a suction operation by the fluid suction unit is performed while ultrasonic vibrations are output from the ultrasonic instrument when the irrigation/suction interlocking mode is selected or when the ultrasonic instrument is an instrument capable of irrigating and sucking the cooling fluid.

4. The ultrasonic treatment apparatus according to claim 1, wherein the irrigation/suction control unit is configured to determine that the ultrasonic instrument is an instrument capable of irrigating and sucking the cooling fluid based on the data on an identifier at the ultrasonic instrument.

5. The ultrasonic treatment apparatus according to claim 2, wherein the irrigation/suction control unit is configured to start driving the fluid irrigation unit immediately after the driving output from the ultrasonic driving control unit has stopped when the irrigation/suction interlocking mode is selected or when the ultrasonic instrument is an instrument capable of irrigating and sucking the cooling fluid.

6. The ultrasonic treatment apparatus according to claim 2, wherein the irrigation/suction control unit is configured to start driving the fluid suction unit immediately after output of the cooling fluid from the fluid irrigation unit has stopped when the irrigation/suction interlocking mode is selected or when the ultrasonic instrument is an instrument capable of irrigating and sucking the cooling fluid.

7. An ultrasonic treatment apparatus comprising:
an ultrasonic instrument configured to treat a living-body tissue through ultrasonic vibrations;
a fluid irrigation unit configured to irrigate a cooling fluid for cooling the ultrasonic instrument to the ultrasonic instrument;
a fluid suction unit configured to suck the cooling fluid irrigated at least by the fluid irrigation unit to the ultrasonic instrument;
an ultrasonic driving control unit configured to control a driving output of the ultrasonic vibrations supplied to the ultrasonic instrument;
a mode switching unit configured to select one of an irrigation/suction interlocking mode in which the ultrasonic driving control unit interlocks with the fluid irrigation unit and the fluid suction unit, and an irrigation/suction non-interlocking mode in which the ultrasonic driving control unit does not interlock with the fluid irrigation unit and the fluid suction unit; and
an irrigation/suction control unit configured to, when the irrigation/suction interlocking mode is selected in the mode switching unit, drive the fluid irrigation unit after the driving output by the ultrasonic driving control unit has stopped and further drive the fluid suction unit after a predetermined period of time has passed after initiation of the drive of the fluid irrigation unit, and, when the irrigation/suction non-interlocking mode is selected in the mode switching unit, control so that the fluid irrigation unit and the fluid suction unit do not operate after the driving output by the ultrasonic driving control unit has stopped.

8. An ultrasonic treatment apparatus comprising:
an ultrasonic instrument configured to treat a living-body tissue through ultrasonic vibrations;
an identifier attached to the ultrasonic instrument configured to store unique information of the ultrasonic instrument;
a detecting unit configured to detect the unique information of the identifier attached to the ultrasonic instrument;
a fluid irrigation unit configured to irrigate a cooling fluid for cooling the ultrasonic instrument to the ultrasonic instrument;
a fluid suction unit configured to suck the cooling fluid irrigated at least by the fluid irrigation unit to the ultrasonic instrument;
an ultrasonic driving control unit configured to control a driving output of the ultrasonic vibrations supplied to the ultrasonic instrument based on a result of detection by the detecting unit regarding the unique information; and
an irrigation/suction control unit configured to, when it is determined based on the result of detection by the detecting unit that an irrigation/suction interlocking mode is selected in which the ultrasonic driving control unit interlocks the fluid irrigation unit and the fluid suction unit, drive the fluid irrigation unit after the driving output by the ultrasonic driving control unit has stopped and further drive the fluid suction unit for after a predetermined period of time has passed after initiation of the drive of the fluid irrigation unit, and, when it is determined based on the result of detection by the detecting unit that an irrigation/suction non-interlocking mode is selected in which the ultrasonic driving control unit does not interlock with the fluid irrigation unit and the fluid suction unit, control so that the fluid irrigation unit and the fluid suction unit do not operate after the driving output by the ultrasonic driving control unit has stopped.

9. A method for operating an ultrasonic treatment apparatus including an ultrasonic instrument, a fluid irrigation unit configured to irrigate a cooling fluid for cooling the ultrasonic instrument to the ultrasonic instrument, and a fluid suction unit configured to suck the cooling fluid irrigated by the fluid irrigation unit to the ultrasonic instrument, the method comprising:
selecting either an irrigation/suction interlocking mode or an irrigation/suction non-interlocking mode;
when the irrigation/suction interlocking mode is selected, sequentially irrigating and suctioning cooling fluid after an ultrasound output of the ultrasonic instrument has stopped; and
when the irrigation/suction non-interlocking mode is selected, not irrigating and suctioning cooling fluid after a driving output of the ultrasonic driving control unit has stopped.

* * * * *